(12) United States Patent
Polonka et al.

(10) Patent No.: US 7,442,674 B2
(45) Date of Patent: *Oct. 28, 2008

(54) BEAUTY WASH PRODUCT COMPOSITIONS DELIVERING ENHANCED VISUAL BENEFITS TO THE SKIN WITH SPECIFIC OPTICAL ATTRIBUTES

(75) Inventors: Jack Polonka, Peekskill, NY (US); Brian Keith Hamilton, Lansdale, PA (US); Alexander Lips, Edgewater, NJ (US); Prem Chandar, Closter, NJ (US); Liang Sheng Tsaur, Norwood, NJ (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/043,509

(22) Filed: Jan. 26, 2005

(65) Prior Publication Data

US 2005/0233916 A1   Oct. 20, 2005

Related U.S. Application Data

(63) Continuation-in-part of application No. 10/996,532, filed on Nov. 24, 2004, now abandoned, which is a continuation-in-part of application No. 10/815,003, filed on Mar. 31, 2004, now abandoned.

(51) Int. Cl.
   *A61K 7/00* (2006.01)
(52) U.S. Cl. .................. 510/130; 510/139; 510/158; 510/424; 510/470; 424/70.1; 424/70.9
(58) Field of Classification Search ............... 510/130, 510/139, 159, 424, 470, 473
   See application file for complete search history.

(56) References Cited

U.S. PATENT DOCUMENTS

| 4,673,525 A | 6/1987 | Small et al. |
| 5,076,953 A | 12/1991 | Jordan et al. |
| 5,296,159 A | 3/1994 | Wilson et al. |
| 5,952,286 A | 9/1999 | Puvvada et al. |
| 6,451,300 B1 | 9/2002 | Dunlop et al. |
| 6,759,376 B2 | 7/2004 | Zhang et al. |
| 6,780,826 B2 * | 8/2004 | Zhang et al. ............ 510/130 |
| 2004/0087668 A1 * | 5/2004 | Schmucker-Castner et al. ............ 516/90 |
| 2004/0186030 A1 * | 9/2004 | Hofrichter et al. ........ 510/130 |
| 2004/0223993 A1 * | 11/2004 | Clapp et al. ............ 424/401 |
| 2004/0234470 A1 | 11/2004 | Zhang et al. |

FOREIGN PATENT DOCUMENTS

WO   97/29736   8/1997

OTHER PUBLICATIONS

U.S. Appl. No. 10/814,473, filed Mar. 31, 2004, Patel et al., (now abandoned), for: Beauty Wash Product Bar Compositons Delivering Enhaced Visual Benefits to the Skin With Specific Optical Attributes.
U.S. Appl. No. 10/997,180, filed Nov. 24, 2004, Patel et al., for: Beauty Wash Product Bar Compositons Delivering Enhaced Visual Benefits to the Skin With Specific Optical Attributes.
U.S. Appl. No. 11/043,315, filed Jan. 26, 2005, Patel et al., for: Beauty Wash Product Bar Compositons Delivering Enhaced Visual Benefits to the Skin With Specific Optical Attributes.
U.S. Appl. No. 10/815,003, filed Mar. 31, 2004, Polonka et al., (now abandoned), for: Beauty Wash Product Compositons Delivering Enhaced Visual Benefits to the Skin With Specific Optical Attributes.
U.S. Appl. No. 10/996,532, filed Nov. 24, 2004, Polonka et al., for: Beauty Wash Product Compositions Delivering Enhanced Visual Benefits to the Skin With Specific Optical Attributes.
U.S. Appl. No. 10/814,879, filed Mar. 31, 2004, Tsaur et al., (now abandoned), for: Rinse-Off Facial Wash Compositions Delivering Enhanced Whitening Using Submicron Titanium Oxide, Optional Modifier and Deposition System.
U.S. Appl. No. 10/997,179, filed Nov. 24, 2004, Tsaur et al., for: Rinse-Off Facial Wash Compositions Delivering Enhanced Whitening Using Submicron Titanium Oxide, Optional Modifier and Deposition System.

* cited by examiner

*Primary Examiner*—Necholus Ogden
(74) *Attorney, Agent, or Firm*—Ronald A. Koatz

(57) ABSTRACT

The present invention relates to compositions delivering enhanced visual benefits to the skin with specific optical attributes. These are delivered using specific deposition systems (where oil/emollient comprises part of deposition system) and/or by ensuring dispersion of particles.

12 Claims, No Drawings

BEAUTY WASH PRODUCT COMPOSITIONS DELIVERING ENHANCED VISUAL BENEFITS TO THE SKIN WITH SPECIFIC OPTICAL ATTRIBUTES

RELATED APPLICATIONS

The present application is a continuation-in-part of application U.S. Ser. No. 10/996,532 to Polonka et al., filed Nov. 24, 2004 now abandoned (adding additional examples), which in turn is a continuation-in-part of U.S. Ser. No. 10/815,003, filed Mar. 31, 2004 now abandoned.

FIELD OF THE INVENTION

The present invention relates to compositions delivering solid particulate optical modifiers (e.g., titanium dioxide, mica, etc.) delivering enhanced visual benefits (gloss, shine, color) to the skin using specific deposition systems capable of delivering the optical modifiers from rinse-off bar compositions to provide specific optical attributes (e.g., to enhance reflectance by certain per cent and/or to change unit lightness or color values in amounts previously not possible in rinse-off systems). Generally, the enhancement is obtained by use of specific deposition system (e.g., cationic polymer/anionic surfactant precipitates and wherein the deposition system also comprises oil/emollient) and/or by ensuring dispersion of particles (e.g., little or no agglomeration) onto skin or deposited substrate.

BACKGROUND

It is extremely difficult to deliver enhanced optical properties (radiance; whiteness; perceived blueness versus yellowness or reds versus green) from a rinse-off composition (e.g., liquid or bar compositions). The optical modifiers delivering these properties are not readily deposited, are readily rinsed of and, because they readily agglomerate, are not in a sufficiently dispersed state to be efficiently delivered to substrate (which is another way to say that they rinse off too easily).

Applicants' co-pending U.S. Ser. No. 10/241,401 to Zhang et al., filed Sep. 11, 2002 discloses personal care formulations comprising particles of defined refractive index, thickness, geometry and size. While this disclosure relates to how size, shape, etc. of the particles themselves help deposition (and thus shine), it fails to disclose specific deposition enhancement systems (e.g. based on type of surfactant and/or polymers), and the use of such systems to deliver specifically targeted optical properties when values defining these targeted properties are changed by certain absolute or percentage amounts. It also does not disclose how particles must be adequately dispersed on substrate (e.g., skin) to deliver defined change values needed to perceive measure optical traits.

U.S. Ser. No.10/443,396 to Zhang et al., filed May 23, 2003 discloses structured benefit agent for enhanced delivery of optical modifier, but again does not disclose specific delivery systems, does not disclose necessity of, or manner to achieve particulate dispersal, and does not disclose compositions or materials needed to deliver change in values (absolute or percentage) associated with perceived optical benefit.

In a related application filed on Nov. 24, 2004, applicants claim compositions for delivery of enhanced visual benefits to skin with specific optical attributes. The claims cover modifiers combined with deposition enhanced system, but do not specifically claim such deposition system must comprise oil/emollient. The subject application adds some additional examples where oil is present in the deposition system. (there are some examples in the related application where oil is used, e.g., bismuth oxychloride is commercially sold as solids suspended in oil such as, for example, castor oil), and further specifically claims such compositions.

In a co-pending application filed same date as the subject application, compositions when oil/emollient comprise part of the deposition system are claimed, but the copending application is directed specifically to bar compositions.

BRIEF SUMMARY OF THE INVENTION

Applicants have now found both compositions and ways to manipulate such compositions to provide specific optical benefits from rinse-off systems. That is, using deposition enhancement systems (e.g., characterized, for example, by precipitates formed through interaction of polymers and surfactants and the use of oil/emollient in the deposition system), modifiers associated with specified optical properties (gloss, whiteness, degree of "blueness") can be dispersed and delivered to provide desired optical attributes (i.e., by providing sufficient change in absolute or percentage values of the components to result in perceived optical changes). Changes in optical attributes previously unobtainable from wash-off/rinse-off systems are provided by selecting the specified components.

More particularly, the invention comprises as follows:

Beauty wash product compositions for delivery of enhanced (changed) visual benefits to the skin with specific optical attributes comprising:

a) from 5.0% to about 90%, preferably 5 to 75%, more preferably 10 to 75% by weight surfactant selected from anionic, nonionic, amphoteric and cationic surfactants and mixtures thereof.

b) from 0.1 to 35%, preferably 0.2 to 25% by weight of solid particulate optical modifier which exhibits a specific set of optical properties (e.g., defining radiance or shine ($\Delta$ gloss), whiteness ($\Delta$ L), degree of red or greenness ($\Delta$ a*), degree of yellow or blueness ($\Delta$ b*), change in opacity) and which, in combination with a deposition enhancement system, provides at least 5% improvement (i.e., 5% change) in at least one visual attribute being targeted (e.g., shine, color), wherein values reflecting various optical properties are measured before or after conducting tests according to a defined protocol, when said composition is applied to the skin;

c) from 0.1 to 25% by wt. of a deposition enhancement system, wherein, the deposition enhancement system enhances delivery to the skin of a target or defined visual attribute (e.g. shine) by the optical modifier relative to a composition that has the same surfactant and optical modifier used at the same concentration but does not have the deposition enhancement system; and d) from about 0.1% to 90%, (preferably 0.1 to 45% for liquids and 0.1 to 80% for bars) of a hydrophilic structural dispersant (e.g., polyalkylene glycol); wherein said deposition enhancement system comprises oil/emollient.

As noted, the changes in visual attribute may be measured by a change in value of at least one component (gloss value, color value defined by an a* or b* value) of at least 5% in absolute or per cent terms.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances b the term "about". Similarly, all percentages are weight/weight percentages of the total composition unless otherwise indicated. Numerical ranges expressed the format "from x to y" are understood to include x and y. When for a specific feature multiple preferred ranges are described in the format "from x to y" it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to composition and to methods of delivering enhancement in delivery of a targeted visual value (e.g., reflectance/shine; opacity/translucency; whiteness; blueness; rosiness) from rinse-off compositions (e.g., bars or liquids). Specifically, by using deposition enhancement systems (specifically, these comprise oil/emollient as part of the deposition enhancement system), the targeted values can be manipulated to deliver the desired attribute or look.

The enhanced attribute can be delivered from a variety of forms which include facial cleansers, rinse-off bathing cleansers and bars.

Specifically, the rinse-off compositions of the invention comprise:
  a) 5.0% 90%, preferably 5% to 75%, more preferably 10 to 75% by wt. of a surfactant or mixture of surfactants;
  b) 0.1% to 35%, preferably 0.2% to 25% by wt. of a solid particulate optical modifier enhancing a specific set of properties (e.g. whiteness) and which, in combination with deposition enhancement system for the modifier (e.g. precipitate formed from interaction of polymer and surfactant) provides at least 5% change in at least one targeted visual attribute, wherein said change is defined by increase or decrease in absolute or percentage value characterizing a specific trait (i.e., ) gloss is associated with radiance or $\Delta L$ with whiteness) and evaluation is made after using a defined in vitro skin protocol test;
  c) from 0.1 to 25% by wt. of said deposition enhancement system wherein, said system (c) is defined by its ability to enhance delivery of said targeted visual attribute, by the modifier relative to composition with some surfactant and modifier at same concentration, but which does not have the deposition enhancement system, and
  d) from 0.1 to 90% by wt. of a hydrophilic structural dispersant;
wherein said deposition enhancement system comprises oil/emollient as part of the system.

In general, the surfactant system used is also not critical. It is, however, preferred that there be present at least one lathering anionic surfactant.

Surfactant is present at a level of 0.5 to 90%, preferably 5 to 75%, more preferably 10 to 75%, even more preferably 20 to 70%, by wt. of composition depending on product form.

In general, as noted, the surfactant may be selected from the group consisting of soap (including pure soap systems), anionic surfactant, nonionic surfactant, amphoteric/zwitterionic surfactant, cationic surfactant and mixtures thereof.

"Soap" is used is in the popular sense i.e., alkali metal or alkanol ammonium salts of aliphatic, alkane or alkene monocarboxylic acids. Other surfactants which may be used are described in "Surface Active Agents and Detergents" (Vol. I & II) by Schwartz, Perry & Berch, a copy of which is incorporated by reference into the subject application.

Bars may include pure soap bars, bars which are primarily (>50% of surfactant system) soap and have some synthetic, bars which are primarily synthetic and have some soap, bars which are primarily sugar based bars, bars which are primarily polyethylene glycol based bars, etc.

With regard to visual attributes targeted by the optical modifier, these attributes may include, but are not limited to, attributes such as skin shine, skin lightness, skin color, skin glow, skin radiance, skin optical uniformity, skin evenness, and combinations thereof.

As indicated, the particulate optical modifier should change provide, in combination with deposition enhancement system, at least a 5% change in a visual attribute being targeted, wherein 5% increase refers to of at least one of various values (L, a*, b* gloss, etc.) which is associated with a particular attribute identified with the value (e.g.; L refers to "whiteness").

Specifically, improvement is measured by taking a value for a particular measured component (for example, gloss value, L value, a* value, b* value) and measuring (e.g. using in in vitro pig assay) values of these components before and after application of particle deposition enhancement system.

Thus, for example, if gloss score changes from 5.5 to 7.8 (or visa versa) (as measured in a gloss meter), there is a percent differential of 41.8% in gloss. Similarly, if "a*" value (measure of rosiness) goes from 2.3 to 0.8, this is an absolute decrease of −1.5, well beyond 5%.

The optical benefit carried by the deposition of optical modifier can be targeted to either plateaus on the skin surface or to skin crevices.

In one embodiment of the invention, in absolute value, the composition of the invention (with modifier and added deposition system relative to composition with no deposition system) deposits modifier to exhibit $\Delta L$ value in range of 0 to ±10 "L" units, wherein said L units are defined by Hunter Lab Color Meter as described in the protocol, reflectance change in range of 0 to about ±300% as defined by a change in measured gloss from a gloss meter; and change in opacity in range from about 0 to ±50% measured in opacity contrast defined as $\Delta L$ divided by 60; wherein, at least one value has a change of at least 5% from the initial value prior to delivery of modifier.

In another embodiment, the formulation deposition of modifier creates a change in skin shine, glow or similar attributes, and the particulate optical modifier deposits to exhibit $\Delta L$ value in range of about 0 to about ±10 L units, reflectance change in the range from 0 to about ±300% change in gloss, and a change in opacity in a range of 0±20%, wherein, $\Delta a*$ and $\Delta b*$ are within normal skin range. Maintaining a normal skin range means that $\Delta a*$ and $\Delta b*$ are <2 $\Delta a*$ or $\Delta b*$ units, respectively, preferably less than 1 unit. Again, there must be a least 5% change in at least one of reflectance, L, or opacity.

In another embodiment, the formulation deposition of modifier creates skin lightening, whitening, and/or color or similar attributes and the composition deposits particulate optical modifier to exhibit $\Delta L$ value in the range of ±10 L units, $\Delta a*$ value in range from about 0 to about ±10, $\Delta b*$ value in range from about 0 to about ±10, and a change in opacity in the range from about 0 to about ±50%. The reflectance is within normal skin reflectancy range. In this case, this means change in reflectance is ≦10%. Here, as noted, there is more of a focus on Δa* and Δb* values since there is a focus on general color attributes.

In yet another embodiment, the formulation creates skin optical uniformity, evenness, blurring, soft focus or similar attributes and the composition deposits particulate optical modifier to exhibit ΔL value in the range of ±5 L units, a reflectance change in the range from about 0 to about ±100% (gloss units) and a change in the opacity in the range from about 0 to about ±50% (defined by ΔL /60), wherein Δa* and Δb* are within normal skin color range. (change of ≦2 a* or b* units respectively)

What is important to note is that the formulation can be formulated to yield a mixture (one or more effects/visual attributes) depending on the exact mixture of particles and/or particle types and/or deposition enhancement. Obtaining specific visual attributes of this kind by manipulating L or a* or b* or gloss value has not been previously possible from a wash-off system.

Specifically, any individual visual effect can be obtained by adjusting the optical space to specifically desired optical space within ranges of, for example, ΔL, Δa*, Δb*, etc. It should be noted, if not already clear, that ranges can be manipulated to obtain effect for one or more attributes or mixtures thereof.

Structurant

The structurant of the invention can be a water-soluble or water insoluble structurant.

Water soluble structurants include moderately high molecular weight polyalkylene oxides of appropriate melting point (e.g. 40° to 100° C., preferably 50° to 90° C.) and in particular polyethylene glycols or mixtures thereof.

Polyethylene glycols (PEG's) which are used may have a molecular weight in the range 2,000 to 25,000 preferably 3,000 to 10,000. However, in some embodiments of this invention it is preferred to include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a large quantity of other water-soluble structurant such as the above mentioned polyethylene glycol of molecular weight 2,000 to 25,000, preferably 3,000 to 10,000.

Water insoluble structurants also have a melting point in the range 40° to 100° C., more preferably at least 50° C., notably 50° C. to 90° C. Suitable materials which are particularly envisage are fatty acids, particularly those having a carbon chain of 12 to 24 carbon atoms. Examples are lauric, myristic, palmitic, stearic, arachidic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkenols of 8 to 20 carbon atoms, particularly cetyl alcohol. These materials generally have a water solubility of less than 5 g/litre at 20° C.

Soaps (e.g. sodium stearate) can also be used at levels of about 1% to 15%. The soaps may be added neat or made in situ by adding a base, e.g. NaOH to convert free fatty acids.

The relative proportions of the water-soluble structurants and water insoluble structurants govern the rate at which the bar wears during use. The presence of the water-insoluble structurant tends to delay dissolution of the bar when exposed to water during use and hence retard the rate of wear.

The structurant is used in the bar in an amount of 20% to 85%, preferably 30% to 70% by wt.

By water soluble is meant generally that 1% or more of compound is soluble in water at room temperature.

Optical Modifier

The optical modifier which may be used for the subject invention may be chosen from non-colored and colored, organic and inorganic materials.

Among the materials which may be used are included:

Organic pigments, inorganic pigments, polymers and fillers such as titanium oxide, zinc oxide, colored iron oxide, chromium oxide/hydroxide/hydrate, alumina, silica, zirconia, barium sulfate, silicates, natural/alkaloid (including derivatives) polymers, polyethylene, polypropylene, nylon, ultramarine, alkaline earth carbonates. The materials can be platy materials such as talc, sericite, mica, synthetic mica, platy substrate coated with organic and inorganic molecules, bismuth oxychloride, barium sulfate. Particle can be composed of several materials (like dyes, lakes, toners). Lakes are, for example, dyes with aluminum hydroxide to help bind to solid. Color can be generated through fluorescence, absorption or iridescence. That is, color of modifier materials is generated through optical means rather than, for example, chemical means.

The optical modifier may also be a UV screen material with a $D_{50}$<100 nanometers (where $D_{50}$ means size of 50% of particles or less is <100→m.

The optical modifiers may also be defined by their physical properties. For example, the optical modifier may be broadly defined as follows:
  i) an exterior surface having a refractive index of 1.3 to 4.0
  ii) a geometry which is spheroidal, platy or cylindrical
  iii) dimensions: spheroidal—0.1 to 200 μm, platy—1 to 200 μm, cylindrical—1 to 200 μm in length and 0.5 to 5.0 μm in diameter
  iv) a $D_{50}$ of ≦200 microns in particle size.
  v) may have fluorescence color, absorption color and/or interference color (color through optics)

More specifically particles providing change in shine/glow/radiance may be defined as follows:
  i) an exterior surface having a refractive index of 1.8 to 4.0
  ii) a geometry which is platy or cylindrical
  iii) dimensions: spheroidal—0.1 to 200 μm (microns), platy—10 to 200 μm, cylindrical—10 to 200 μm in length and 0.5 to 5.0 μm in diameter
  iv) a $D_{50}$ of ≦200 μm in particle size.

Particle providing skin lightening/color may be defined as follows:
  i) an exterior surface having a refractive index of 1.3 to 4.0
  ii) a geometry which is spheroidal or platy
  iii) dimensions: spheroidal—0.1 to 1 μm, platy—1 to 30 μm,
  iv) a $D_{50}$ of ≦300 μm in particle size.
  v) may have fluorescence color, absorption color and/or interference color (color through optics)

Particle-producing evenness or soft focus may be defined as follows:

i) an exterior surface having a refractive index of 1.3 to 2.0
ii) a geometry which is spheroidal, platy or cylindrical
iii) dimensions: spheroidal—0.1 to 200 μm, platy—1 to 10 μm, cylindrical—1 to 10 μm in length and 0.5 to 5.0 μm in diameter
iv) a $D_{50}$ of $\leqq 200$ μm in particle size.

Of course, the formulation can contain a mixture of particles, each containing characteristics of a specific visual benefit, to create a combination of visual effects.

It is also to be understood that for visual effects/attributes to have maximum effect, the particles have to be well dispersed on the skin and should also give minimal to no sensory negatives.

By being "well dispersed" is meant that the particles should not agglomerate and that they should be spread easily through the skin surface.

In a preferred embodiment, less than 30% of particles are agglomerates having a size of ten times or more than the $D_{50}$ particles size. This can be measured using optical or electron microscopy.

The particle is used at about 0.1% to 35% by weight preferably 0.2 to 25% by wt., of the composition.

Deposition Enhancement

The deposition enhancement is key to the delivery of particles providing enhanced visual benefit (e.g., as defined in changes in ΔL, Δa*, etc. and in methods to manipulate the values to provide the desired benefit, e.g. radiance, color, etc.).

In one embodiment, the deposition is provided by a deposition system comprising as follows:

a) from about 0.1 to about 10% by wt., preferably 0.1 to 8% by wt. of a cationic polymer having change density $\geqq 1$ Meq/gram, and
b) about 0.1 to 30% by wt., preferably 0.5% to 25% by wt. of an anionic surfactant which forms a precipitate with cationic polymer upon dilution; and
c) 0.1 to 40% oil/emollient which comprises part of the deposition enhancement system.

The precipitate formed can be a floc which can be broken up upon shear or rubbing to form a uniform and dispersed film on the surface of the skin.

Example of such surfactants include $C_{10}$-$C_{24}$ fatty acid soaps (e.g., laurates), alkyl taurate (e.g., cocoyl methyl taurate or other alkyl taurates), sulfosuccinates, alkyl sulfates, glycinates, sarcosinates and mixtures thereof.

It is important that the cationic have the noted charge in order to form the precipitate which is a key to the deposition of optical modifiers delivering the desired optical attributes. The polymers may be modified polysaccharides including cationic guar gums, synthetic cationic polymers, cationic starches, etc.

Specific cationic polymers which are to be used include Merquat® polymers such as polyquaternium 6 (e.g., Merquat®100 or Salcare®SC30) and polyquaterium7 (e.g. Merquat®2200 or Salcare®SC10); guar gums and/or derivatives (e.g. Jaguar C17); quaternized vinylpyrrolidone/methacrylate copolymers (e.g., Gafquat® 775); and polyquaternium-16 (e.g.; Luviquat®FC550)

Specific examples of polymers and their charge densities are listed in the Table below.

| Type of Polymer | TradeName | Company | Charge Density (meg/g) |
|---|---|---|---|
| Guar | | | |
| Guar hydroxypropyltrimonium chloride | Jaguar C17 | Rhodia | >Jaguar C13S |
| Hydroxypropyl guar hydroxypropyltrimonium chloride | Jaguar 162 | Rhodia | −Jaguar C13S |
| Guar hydroxypropyltrimonium chloride | Jaguar C13S | Rhodia | 0.8 |
| Guar hydroxypropyltrimonium chloride | Jaguar C14S | Rhodia | ~Jaguar C13S |
| Guar hydroxypropyltrimonium chloride | Jaguar Excel | Rhodia | ~Jaguar C13S |
| Guar hydroxypropyltrimonium chloride | N-Hance 3000 | Hercules | 0.41 |
| Guar hydroxypropyltrimonium chloride | N-Hance 3196 | Hercules | 0.72 |
| Guar hydroxypropyltrimonium chloride | N-Hance 3215 | Hercules | 1.05 |
| Synthetics | | | |
| Polyquaternium-6 | Merquat 100 | Ondeo Nalco | 6.2 |
| Polyquaternium-7 | Merquat 2200 | Ondeo Nalco | 3.1 |
| Polyquaternium-7 | Merquat 550 | Ondeo Nalco | 3.1 |
| Polyquaternium-7 | Merquat S | Ondeo Nalco | 3.1 |
| Polyquaternium-7 | Salcare Super 7 | Ciba | 1.5 |
| Polyquaternium-7 | SalcareSC10 | Ciba | 4.3 |
| Polyquaternium-7 | Salcare SC11 | Ciba | 3.1 |
| Polyquaternium-6 | Salcare SC30 | Ciba | 6.2 |
| Polyquaterniumj-16 | Luviquat FC370 | BASF | 2 |
| Polyquaterniumj-16 | Luviquat FC550 | BASF | 3.3 |
| Polyquaterniumj-16 | Luviquat FC552 | BASF | 3 |
| Polyquaterniumj-16 | Luviquat FC905 | BASF | 6.1 |
| Polyquaternium-44 | Luviquat MS370 | BASF | 1.4 |
| Cationic Cellulose Derivatives | | | |
| Polyquaternium-4 | Celquat H-100 | National Starch | 0.71 |
| Polyquaternium-4 | Celquat L-200 | National Starch | 1.43 |
| Polyquaternium-4 | Celquat SC230M | National Starch | 1.36 |

-continued

| Type of Polymer | TradeName | Company | Charge Density (meg/g) |
|---|---|---|---|
| Polyquaternium-4 | Celquat SC240C | National Starch | 1.29 |
| Polyquaternium-4 | UCARE Polymer JR | Dow Amerchol | 1.3 |
| Polyquaternium-4 | UCARE Polymer JR | Dow Amerchol | 0.7 |
| Dextran Derivatives | | | |
| Dextran hydroxypropylammonium chloride | CDC | Meito Sangyo | 1.6 |

The oil/emollient which comprises part of deposition system can be, for example, silicone, castor oil, sunflower seed oil.

Preferably, by comprising part of the deposition system is meant that the deposited particle may be enveloped/surrounded by the oil and/or be part of an emulsion system in which deposited particles are emulsified in the oil/emollient, or becomes enveloped/surrounded during dilution with water.

One example of such particles suspended in oil, for example, is bismuth oxychloride suspended in castor oil (e.g., Rona® Biron Silver, a 70% solids suspension in castor oil). Such solution was used in the parent application of the subject application, filed Nov. 24, 2004 (see, for example, Formulation 6 or 7) as well as in the grandparent application, filed Mar. 31, 2004.

In general, other deposition aids (e.g., for the optical modifier particles) may include granular anionic polymers (e.g. alkaloid polymer such as starch, cellulose or their derivatives). That is, if the deposition system additionally comprises such deposition aid, results are further enhanced. Incorporation of the emollient as part of the deposition system as noted above boosts the deposition system. The enhancement would generally be, for example, at least 10% in some value (e. g., gloss, $\Delta L$, $\Delta a^*$ or $\Delta b^*$) relative to if no emollient is added to the deposition system at all.

It should be further noted that oils/emollients may be used which are not specifically associated with deposition and which are added for sensory (e.g., tactile) effect. Among oils which may be used are included, for example, vegetable oils such as orachis oil, castor oil, cocoa butter, coconut oil, corn oil, cotton seed oil, palm kernel oil, rapeseed oil, sunflower seed oil, safflower seed oil, sesame seed oil and soybean oil.

Emollients may include the vegetable oils noted above and may further comprise esters, fatty acids, alcohols, polyols and hydrocarbons. Esters may be mono-or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate and co-caprate, propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds.

For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Yet, another way to enhance deposition may be through modification (e.g. surface modification) of particles.

In another embodiment, the deposition enhancement system may comprise:
1) from 0.1 to 10% by wt. of an anionic polymer having charge density of at least $\geq 1.0$ Meq/gram; and
2) from about 0.1 to 30% cationic surfactant which forms a precipitate with the anionic polymer upon dilution;
3) 0.1 to 40.0% by wt. oil/emollient.

This system is the inverse of cationic polymer anionic surfactant system. The precipitate can also be a floc which can be broken up on shear or rubbing and form a uniform and dispersed film on the skin surface.

Cationic surfactant may be a quaternary amino surfactant or an amphoteric such as betaine (e.g., cocoamidopropyl betaine).

The anionic polymer may be a polyacrylate, cross-linked polyacrylate, polyurethane and/or alkaloid derived polymer (e.g., starch, cellulose and derivatives), polysaccharide (e.g. xanthan gum), agar and/or mixtures thereof.

Oils/emollients may include any of those discussed above.

This system may also additionally comprise 0.1 to 30% granular anionic polymer which is natural alkaloid polymer (starch, cellulose and derivatives) as deposition aid.

EXAMPLES

Protocol

In Vitro Porcine/Pig Skin Assay

A piece of black porcine skin is used (L=40±3), where skin has dimensions of 5.0 cm by 10 cm, and the skin is mounted on black background paper card. Initial measurements of untreated skin are made. The mounted skin is then washed and rinsed with 0.2 g of liquid wash-off formulation or soap bar. After two (2) hours of drying, final measurements are made Color Measurements Initial and final color measurements were made of porcine or in-vivo human skin using a Hunter Lab spectra colormeter using a 0° light source and 45° detector geometry. The spectra colormeter was calibrated with the appropriately black and white standards. Measurements were made before and after wash treatment. Three measurements were made each time and averaged. Values of L, a*, and b*, which came from the L a* b* color space representation, were obtained in this manner. L measures units of "Lightness", a* measures values from red to green and b* measures values from yellow to blue.

Reflectance (Gloss) Determination

Initial and final reflectance/radiance measurements of porcine or in-vivo human skin was made with a gloss meter which measures units of gloss. The gloss meter was first set with both detector and light source at 85° from normal. The gloss meter was calibrated with appropriate reflection standard. Measurements of gloss were taken before and after application of formulation and Δ gloss was calculated to obtain percent difference.

Opacity Determination

Opacity of washable deposition was calculated from Hunter Lab color measurements. Opacity contrast was calculated ΔL (change in whiteness after deposition compared to prior to deposition) divided by 60 (which is the difference in L value of skin and a pure white color).

Examples 1-5

The following compositions show changes in value (i.e. ) gloss (%), ΔL, Δ a*, Δ b*, as seen at bottom of chart) when surfactant and deposition systems are used relative to compositions either without same ingredients and/or with different or no deposition systems.

| Pigment-Containing Compositions | | | | | |
|---|---|---|---|---|---|
| Component | Ex. 1 | Ex. 2 | Ex. 3 | Ex. 4 | Ex. 5 |
| Lauric/Myristic/Palmitic/Stearic acid (fatty acids) | 3.27/5.37/7.12/6.24/3.91 KOH | | | | |
| Sodium N-cocoyl N-methyl taurate (30%) (surfactant) | 6.0 | | | | |
| 20EOcetylether/dipropyleneglycol/ glycerin/maltitol solution(75%) (sensory) | 4/8.8/12/4 | | | | |
| Dibutylhydroxytoluene/EDTA | 0.05/0.05 | | | | |
| Jaguar C13S (Cationic Polymer) | 0.4 | 0.4 | 0.4 | 0.4 | 0.4 |
| Titanium Dioxide (Kronos 2071-U, 0.3 to 0.5 um) | 20 | 10 | 10 | 10 | 10 |
| Metal soap treated Talc (J68MT, <10 um, US cosmetic Corporation) | — | — | 5 | — | — |
| Mica (TiO2 coated mica, <15 um, Timiron MP1005 from Rona) | — | — | — | 5 | — |
| Mica22 (22 um, Cardre Inc.) | — | — | — | — | 5 |
| Petrolatum | — | — | — | — | — |
| Neosil CP10 (Crossfield, silica gel 50 to 200 um as exfoliate) | — | — | — | — | — |
| Perfume | 0.25 | 0.25 | 0.25 | 0.25 | 0.25 |
| Deionized water | To 100 | To 100 | To 100 | To 100 | To 100 |
| Pig Skin in vivo | | | | | |
| Δ gloss (%) | −39.8 | −20.8 | 0 | 16.6 | 34.3 |
| Δ L | 19.3 | 7.6 | 7.9 | 7.8 | 14.5 |
| Δ a* | −0.7 | −0.5 | −0.3 | −0.1 | −1.5 |
| Δ b* | −8.3 | −5.7 | −6.7 | −7.5 | −6.7 |

For top 4 rows, same ratios used for all 5 examples.

As seen from the Table above, systems of the invention create optical attributes (ΔL, Δ a*, etc.) which vary in change of the value (and accordingly with the attribute which is highlighted) depending on exact particle, size of particle, and deposition system used. Thus, applicants are able to manipulate values from a wash-off system; and to provide values and the ability to manipulate previously unknown.

A more detailed discussion of observations which can be made from the many examples is set forth below:

Examples 1 to 5, are Jaguar C13S based formulations, which show some deposition.

Examples 1 and 2 have 20% $TiO_2$ and 10% $TiO_2$, respectively, with the 20% TiO2 formulation showing higher deposition and larger ΔL change. There is also a large (and negative) change in the b* value (becoming bluer) The deposition also has a matting visual effect as can be seen from the negative Δgloss (which indicates a lowering of shine).

Examples 3 to 5 use Example 2 formulation with an addition of a reflective particle material.

Example 3 has talc ($D_{50}$ of 10 um) included into the formulation. The slight reflectivity of talc counteracts the matting effect of the deposited TiO2, as can be seen by the zero change in Δgloss. This combination gives a whiter, lighter appearance while still maintaining the skin's normal shine. The addition of the talc did not alter the ΔL or Δb* seen from Example 2.

Example 5 is the same as Example 3 except that natural mica ($D_{50}$ of 22 um) is used. The higher reflectivity of the larger sized mica counteracts the matting effect of the deposited $TiO_2$ and increases the visual shine, as can be seen by the increase in Δgloss. The addition of the natural mica did not alter the ΔL or Δb* seen from Example 2.

Example 4 is the same as Example 3 except that a titan coated mica ($D_{50}$ of 6 um) is used. The greater reflectivity of the titan-coated mica counteracts the matting effect of the deposited $TiO_2$ and increases the visual shine, as can be seen by the increase in Δgloss. The addition of the coated mica does increase the ΔL or Δb* as compared to Example 2.

The control is for comparison purposes. It has the same formulation as Example 2 except there is no cationic polymer (Jaguar C13S). From the L, a*, b*, and gloss values, no deposition is observed.

From Examples 1 to 5, changes in visual attributes can be seen but they are not large enough. The particle deposition needs to be larger. For this to occur, a cationic polymer with a larger charge density must be used (in this case Merquat 100).

Example 6 is the same as Example 2, except the cationic polymer used is Merquat 100. As can be seen from the ΔL and Δgloss, the deposition of the TiO2 is much greater (by a factor of 5). The visual effect is a much greater whiteness but also a larger increase in mattness. To counteract the mattness, natural mica or talc can be added to the formulations.

Example 7 and 8 are Merquat 100 formulations with natural mica or talc. Both examples show an attenuation in the matting effect of the large TiO2 deposition as can be seen by the lower negative or even positive Δgloss.

Starch Structuring

The facial wash-off formulation can also use a different hydrophilic structural dispersent, such as starch. Similar correlations and trends can be seen with the starch formulation system as with the previous examples.

Example 12 and Example 11 compare the deposition of TiO2/talc from formulations using Jaguar C13S and Merquat 100, respectively. As before, the higher charge density Merquat shows greater deposition that Jaguar, with similar visual attributes.

Example 9 is a control formulation, with no cationic polymer. From the L, a*, b*, and gloss measurements, there is little to no deposition.

Example 10 shows the importance of compatibility of surfactant systems to deposition efficiency. Example 10 uses a mixture of CAP Betaine and LE(2)S. In comparison with Example 11, the deposition is less efficient as seen from the lower ΔL values. This is an indication that the CAP Betaine/LE(2)S surfactant system is not as effective at precipitating cationic polymer upon dilution.

Example 6

The chart below provides additional examples.

Pigment-Containing Compositions

| Component | Ex. 6 |
| --- | --- |
| Lauric acid | 3.27 |
| Myristic acid | 5.37 |
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Sorbitol | — |
| Maltitol solution (75%) | 4 |
| Dibutylhydroxytoluene | 0.05 |
| EDTA tetrasodium tetrahydrate | 0.05 |
| Jaguar C13S (Cationic Polymer) | — |
| Merquat 100 (Cationic Polymer) | 0.4 |
| Titanium Dioxide (0.3 to 0.5 um) | 10 |
| UV TiO2 (Treated) | — |
| UV TiO2 (M212, Presperse) | — |
| Petrolatum | |
| Perfume | 0.25 |
| Deionized water | To 100 |
| Pig skin in-vitro | |
| Δ gloss (%) | −50.0 |
| Δ L | 34.6 |
| Δ a* | −2.4 |
| Δ b* | −8.6 |

Again, it can be seen from the above chart how deposition system and particles of invention provide compositions with desired values providing desired optical attributes (e.g., radiance, color, shine)

Control

The chart below provides control example with no cationic.

| Component | Control |
| --- | --- |
| Lauric acid | 3.27 |
| Myristic acid | 5.37 |
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Maltitol solution (75%) | 4 |
| Dibutylhydroxytoluene | 0.05 |
| EDTA tetrasodium tetrahydrate | 0.05 |
| Jaguar C13S | 0 |
| Polymer JR | |
| Merquat 100 | — |
| Titanium Dioxide (0.3 to 0.5 um) | 10 |
| Timiron Super blue | — |
| Petrolatum | — |
| Perfume | 0.25 |
| Deionized water | To 100 |
| Pig skin in-vitro | |
| Δ gloss (%) | −3.9 |
| Δ L | 0.1 |

-continued

| Component | Control |
| --- | --- |
| Δ a* | 0.1 |
| Δ b* | 0.1 |

Again, it can be seen from the control that when there is no cationic, there is little or no deposition.

Example 7

The chart below again shows different variations.

Pigment-Containing Compositions

| Component | Ex. 7 |
| --- | --- |
| Lauric acid | 3.27 |
| Myristic acid | 5.37 |
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Maltitol solution (75%) | 4 |
| Dibutylhydroxytoluene | 0.05 |
| EDTA tetrasodium tetrahydrate | 0.05 |
| Jaguar C13S | — |
| Merquat 100 | 0.8 |
| Titanium Dioxide (PW liquid TiO2, 0.3 um) | 10 |
| UV TiO2 (M212) | — |
| Mica (TiO2 coated mica, <50 um, Timiron super blue from Rona) | — |
| Mica22 (22 um, Cardre Inc.) | 5 |
| Petrolatum | — |
| Perfume | 0.25 |
| Deionized Water | To 100 |
| Pig skin in-vitro | |
| Δ gloss (%) | 20.0 |
| L | 33.03 |
| A* | −3.8 |
| B* | −9.55 |

Example 8

The chart below shows 1 more examples.

| Component | Ex. 8 |
| --- | --- |
| Lauric acid | 3.27 |
| Myristic acid | 5.37 |
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Maltitol solution (75%) | 4 |
| Dibutylhydroxytoluene | 0.05 |
| EDTA tetrasodium tetrahydrate | 0.05 |
| Merquat 100 | 0.4 |
| Titanium Dioxide | 10 |
| Soft Talc | 5 |
| DI Water | To 100 |
| Petrolatum | 10 |

-continued

| Component | Ex. 8 |
|---|---|
| Perfume | 0.25 |
| DI water | To 100 |
| Pig skin in-vitro | |
| Δ gloss (%) | −5.6 |
| L | 31.3 |
| A* | −3.6 |
| B* | −8.0 |

The −5.6 shows a somewhat neutral gloss and counteracts the matting effect of the $TiO_2$.

Examples 9-12

The chart below shows examples with Starch Structured liquids.

| Component | Ex. 9 | Ex. 10 | Ex. 11 | Ex. 12 |
|---|---|---|---|---|
| K Laurate | 6 | — | 6 | 6 |
| Na cocoyl methyl taurate | 3 | — | 3 | 3 |
| Lauryl ether sulfate | 0 | 6 | 0 | 0 |
| Cocoamidopropl Betaine | — | 3 | — | — |
| Corn starch | 10 | 10 | 10 | 10 |
| Co-water soluble cross-linked starch | 1.5 | 1.5 | 1.5 | 1.5 |
| Glycerin | 6 | 6 | 6 | 6 |
| Jaguar C13S | — | — | — | 0.4 |
| Merquat 100 | — | 0.4 | 0.4 | — |
| TiO2 | 15 | 15 | 15 | 15 |
| Soft Talc | 5 | 5 | 5 | 5 |
| Petrolatum | 5 | 5 | 0 | 0 |
| Sunflower seed oil | — | — | — | — |
| Pig skin in-vitro | | | | |
| Δ gloss (%) | −21.4 | −24.6 | −26.4 | 0.0 |
| L | 4.7 | 21.3 | 44.3 | 15.7 |
| A* | −0.5 | −5.2 | −5.8 | −4.23 |
| B* | 4.0 | 10.9 | −10.6 | −11.0 |

Example for Bars

Formulations for Bar referred to as Formulation 1 to 7 are set forth below.

Formulation 1:

60% Talc in pure soap bar wherein soap is a mixture of 15-20% coconut oil and 80 to 85% tallow. Basically, such a mixture has about 95% $C_{12}$ to $C_{18}$ fatty acids

| Formulation 2: | Ingredient | % by weight |
|---|---|---|
| | Polyethylene glycol - 8K | 43.5% |
| | Cocoamidosulfosuccinate | 30% |
| | Fatty Acid | 10% |
| | Sunflower Seed Oil | 10% |
| | Merquat ® cationic | 1.5% |
| | Water | 5% |
| | TiO2 | 16% |

In formulation 2, the cocoamidosulfosuccinate and Merquat are primary deposition aids. The sunflower seed oil is believed to be sensory, but not to significantly enhance deposition (see % gloss figures of −45.1 and −44.6 in Table). Further, $TiO_2$ is not an oil emulsion so no further deposition enhancement is seen from oil being part of the deposition system.

| Formulation 3: | Ingredient | Ingredient |
|---|---|---|
| | Sugar (sucrose) | 45% |
| | Maltodextrin | 15% |
| | Sodium Laurate | 15% |
| | Sodium dodecyl sulfate | 2% |
| | Merquat ® cationic | 0.4% |
| | TiO2 | 10% |
| | H2O | to balance |

Similar to Example 2, cationic and anionic surfactant provide most or all deposition enhancement and $TiO_2$ adds little to deposition.

Formulation 4—same as Formulation 2, but with 10% $TiO_2$ coated with mica instead of $TiO_2$.

As seen mica coating enhances reflectance and whiteness.

Formulation 5—same as Formulation 3, but with 10% $TiO_2$ coated with mica instead of $TiO_2$.

Formulation 6—same as Formulation 2, but with 10% bismuth oxycholride (Rona Byron Silver, a 70% solids suspension in castor oil) instead of $TiO_2$.

In this formulation, the oil (castor oil emulsion of bismuth oxychloride) is part of the deposition system. Comparing Formulation 6 to 2 (Examples 23 and 24 to 15 and 16), it can be seen deposition (and % gloss) is significantly enhanced.

Formulation 7—same as Formulation 3, but with 10% bismuth oxycholride instead of $TiO_2$.

Similar to Formulation 6 relative to 2, when bismuth emulsified in oil (as part of deposition system) is used (see 26 and 27 versus 17 and 18), deposition (reflected in % gloss) is significantly enhanced.

Formulation 8—same as Formulation 5, but with 2% sodium lauryl ether sulfate (SLES) instead of sodium dodecyl sulfate (SDS).

Formulation 9—same as Formulation 5, but with 2% alpha olefin sulfonate (AOS) instead of sodium dodecyl sulfate (SDS).

Examples 13-30

In the Table below are found examples of bars with optical modifier structured in different ways.

| | | | | Delta | | |
|---|---|---|---|---|---|---|
| Examples | Formulation | Description | % Gloss | L | a | b |
| 13 | 1 | 60% talc | −7.9 | 0.3 | 0.1 | 0.0 |
| 14 | 1 | | 21.6 | −0.3 | −0.7 | −0.4 |
| 15 | 2 | | −45.1 | 20.3 | −1.4 | −4.0 |
| 16 | 2 | | −44.6 | 27.5 | −1.8 | −7.2 |
| 17 | 3 | | −12.9 | 2.5 | 0.1 | −4.0 |
| 18 | 3 | | 0.0 | −0.7 | −1.1 | 15.0 |
| 19 | 4 | | 50.0 | 7.0 | −1.2 | −4.9 |
| 20 | 4 | | 93.6 | 10.4 | −1.3 | −5.3 |
| 21 | 5 | | 15.0 | 2.6 | −0.5 | −1.4 |
| 22 | 5 | | 74.7 | 8.6 | −1.3 | −3.8 |
| 23 | 6 | | 110.8 | 3.2 | −0.7 | −1.6 |
| 24 | 6 | | 81.9 | 1.5 | −1.1 | −1.9 |
| 25 | 7 | | 32.2 | 0.4 | −1.3 | −2.4 |
| 26 | 7 | | 19.2 | 2.8 | −0.7 | −1.2 |
| 27 | 8 | | 3.28 | 0.05 | −0.21 | −1.73 |
| 28 | 8 | | 12.25 | 0.79 | 0.44 | 0.76 |
| 29 | 9 | | 33.0 | 1.41 | −0.84 | −0.68 |
| 30 | 9 | | 56.6 | 1.13 | −0.81 | −1.63 |

A brief explanation of examples is indicated below:

From examples 15 to 26, the data shows that the new deposition system (cationic polymer/anionic surfactant) has significant amount of deposition that leads to large changes visual appearance and attributes.

Examples 15, 16, 17 and 18 (sugar and PEG bars) have a high deposition of $TiO_2$ and have the ability to increase whiteness and opacity (hiding power) in a person's appearance.

Examples 19, 20, 21 and 22 show an increase in reflectance and whiteness using tiania coated mica. The effects are similar to examples 7 and 8, except now there is radiance.

Examples 23, 24, 25 and 26 (sugar and PEG bars), with BiOCl, Have a large increase in reflectance/radiance with little increase in whiteness.

Examples 13 and 14 (85/15 bar with 60% talc) however is a case of minimal/poor deposition. It shows minimal whitening and reflectance, even though it contains 60% talc. The other sugar and PEG bar examples have only 10% particle composition. Example 27 and 28 are sugar bars with titania coated mica with a different surfactant (SLES). As compared to Examples 19, 20,21, 22; these examples show lower/poor deposition and visual effect (reflectance).

Example 29 and 30 are sugar bars with titania coated mica with another different surfactant (AOS). The deposition and visual/reflectance results are intermediate between those using SDS and SLES.

Examples 31, 32, and 33

The following soap bars were made and are discussed further below.

Example 31

| Ingredient | % by wt. |
| --- | --- |
| Soap (85/15 tallow/palm kernel oil) | 52.51 |
| Sunflower oil | 10.40 |
| Sugar | 15.60 |
| Mica (Timiron MP-115) ® | 10.40 |
| Water | 9.53 |
| Perfume | 1.56 |

Example 32

| Ingredient | % by wt. |
| --- | --- |
| Soap (85/15 tallow/palm kernel oil) | 57.10 |
| Sunflower oil | 6.00 |
| Silicone (5000 Cs) | 6.00 |
| Glycerin | 6.00 |
| Mica (Timiron MP-115) ® | 10.00 |
| Water | 13.39 |
| Perfume, Minors | ~1.51 |

Example 33

| Ingredient | % by wt. |
| --- | --- |
| Soap (85/15 tallow/palm kernel oil) | 68.15 |
| Glycerin | 1.50 |
| Sunflower oil | 4.00 |
| Mica (Timiron MP-115) ® | 4.98 |
| Glycerin Monostearate | 1.50 |
| Cationic (Merquat 100) | 3.40 |
| CTAC (cetyl trimethylammonium chloride) | 0.40 |
| Water | 14.55 |
| Perfume and other minors | ~1.56 |

| | Optical Effect | | | |
| --- | --- | --- | --- | --- |
| | ΔL | | % Δ Gloss | |
| Example | Direct Contact | Lather Contact | Direct Contact | Lather Contact |
| 31 (Comparative) | 1.7 | 1.5 | 19 | 38 |
| 32 | 1.1 | 1.6 | 4 | 50 |
| 33 | 2.5 | 7.7 | 34 | 71 |

From Examples 31-33 above, several observations may be made.

Example 31 uses sunflower oil as an emollient although, by itself it may not be an extremely efficient deposition aid. When silicone is added to be a part of the deposition system (Example 32), it can be seen from gloss data that deposition is increasing (i.e., from % Δ gloss of 38 to 50). Neither Examples 31 and 32 have cationic deposition polymer.

Finally, Example 33 shows that when both the deposition system has oil/emollient as part of the deposition system, and there is cationic deposition polymer; then shine enhances significantly (% Δ gloss 71), even at lower oil levels (only 4% sunflower).

We claim:

1. A rinse-off bar or liquid composition for delivery of enhanced visual benefits to the skin with specific optical attributes consisting of:
   a) from about 0.5% to about 90% by wt. surfactant system comprising $C_{10}$-$C_{24}$ fatty acids, alkyl taurates, and oxyalkylene ethers;
   b) from 0.1 to 35% by wt. of solid particulate optical modifier which exhibits a specific set of optical properties, defined by ΔL, Δa*, Δb*, change in reflectivity and/or change in opacity, and which, in combination with a deposition enhancement system, provides at least 5% change in at least one of said optical properties being targeted when said composition is applied to the skin;
   c) from 0.1 to 25% by wt. of a deposition enhancement system comprising (i) 0.1 to 10% by wt. of a cationic polyquaternium 6 polymer or polymers having an average charge density of about 6.2 meq/g; and (ii) anionic surfactant and optionally (iii) about 0.1 to 30% by wt. of a granular anionic polymer which is a natural alkaloid polymer which forms precipitate with said cationic polymer or polymers upon dilution and selected from the group consisting of $C_{10}$ to $C_{24}$ fatty acid soap, alkyl taurates, and mixtures thereof; and d) from about 0.1 % to 90% of a hydrophilic structural dispersant comprising alkylene glycol, maltitol and glycerin;

wherein the deposition enhancement system further comprises oil/emollient enveloping/surrounding said optical modifier; and/or comprises oil/emollient which forms an emulsion system in which optical modifier particles are emulsified in the oil/emollient or are enveloped by the oil/emollient during dilution with water.

2. A composition according to claim 1, wherein the optical attribute affected by change of at least 5% in at least one of said optical properties is chosen from skin shine, skin lightness, skin color, skin glow, skin radiance, skin optical uniformity, skin evenness and mixtures thereof.

3. A composition according to claim 1, wherein said optical modifier is a non colored or colored organic or inorganic material selected from organic pigments; inorganic pigments; polymers and fillers in turn selected from: titanium dioxide; zinc oxide; colored iron oxide; chromium oxide, hydroxide or hydrate; alumina; silica; zirconia; barium sulfate; silicates; alkaloid polymers and derivatives thereof; polyalkylene; nylon; ultramarine; alkaline earth carbonate; talc; sericite; natural and synthetic mica; platy substrate coated with organic and inorganic materials; bismuth oxychloride; and mixtures thereof;

4. A composition according to claim 1, wherein said optical modifier is a UV sunscreen material with a $D_{50}$ <100 nanometers.

5. A composition according to claim 1, wherein the oil/emollient which is part of the deposition system is separately prepared as an emulsion and the separately prepared emulsion is mixed with the composition at a separate time.

6. A composition according to claim 1, wherein the oil/emollient which is part of the deposition system is added separately and the particle/oil emulsion is formed during dilution of the composition.

7. A composition according to claim 5, wherein particulate optical modifier is bismuth oxychloride and oil is castor oil.

8. A composition according to claim 1, wherein said polymer is starch and derivatives, cellulose and derivatives and mixtures thereof;

9. A rinse-off bar or liquid composition for delivery of enhanced visual benefits to the skin with specific optical attributes consisting of:
(a) from about 0.5% to about 90% of by wt. surfactant system comprising alkyl sulfatell and betaine;
(b) from 0.1 to 35% by wt. of solid particulate optical modifier which exhibits a specific set of optical properties, defined by ΔL, Δa*, Δb*, change in reflectivity and/or change in opacity, and which, in combination with a deposition enhancement system, provides at least 5% change in at least one of said optical properties being targeted when said composition is applied to the skin;
(c) from 0.1 to 25% by wt. of a deposition enhancement system comprising (i) 0.1 to 10% by wt. of a polyguaternium 6 cationic polymer or polymers having an average charge density of about 6.2 meq/g; and (ii) anionic surfactant which forms precipitate with said cationic polymer or polymers upon dilution and wherein said anionic is alkyl sulfate; and
(d) from about 0.1% to 90% of a hydrophilic structural dispersant, glycerin and starch;
wherein the deposition enhancement system further comprises oil/emollient enveloping/surrounding said optical modifier; and/or comprises oil/emollient which forms an emulsion system in which optical modifier particles are emulsified in the oil/emollient or are enveloped by the oil/emollient during dilution with water.

10. A rinse-off bar or liquid composition for delivery of enhanced visual benefits to the skin with specific optical attributes consisting of:
(a) from about 0.5% to about 90% of by wt. soap and optionally a taurate;
(b) from 0.1 to 35% by wt. of solid particulate optical modifier which exhibits a specific set of optical properties, defined by ΔL, Δa*, Δb*, change in reflectivity and/or change in opacity, and which, in combination with a deposition enhancement system, provides at least 5% change in at least one of said optical properties being targeted when said composition is applied to the skin;
(c) from 0.1 to 25% by wt. of a deposition enhancement system comprising (i) 0.1 to 10% by wt. of a polyquaternium 6 cationic polymer or polymers having an average charge density of about 6.2 meq/g; and (ii) anionic surfactant which forms precipitate with said cationic polymer or polymers upon dilution and selected from the group consisting of soap, alkyl taurate and mixtures thereof; and
(d) from about 0.1% to 90% of a hydrophilic structural dispersant comprising glycerin and starch;
wherein the deposition enhancement system further comprises oil/emollient enveloping/surrounding said optical modifier; and/or comprises oil/emollient which forms an emulsion system in which optical modifier particles are emulsified in the oil/emollient or are enveloped by the oil/emollient during dilution with water.

11. A rinse-off bar or liquid composition for delivery of enhanced visual benefits to the skin with specific optical attributes consisting of:
(a) from about 0.5% to about 90% of by wt. surfactant system comprising fatty acids, and
sulfosuccinates;
(b) from 0.1 to 35% by wt. of solid particulate optical modifier which exhibits a specific set of optical properties, defined by ΔL, Δa*, Δb*, change in reflectivity and/or change in opacity, and which, in combination with a deposition enhancement system, provides at least 5% change in at least one of said optical properties being targeted when said composition is applied to the skin;
(c) from 0.1 to 25% by wt. of a deposition enhancement system comprising (i) 0.1 to 10% by wt. of a polyquaternium 6cationic polymer or polymers having an average charge density of about 6.2 meq/g; and (ii) anionic surfactant which forms precipitate with said cationic polymer or polymers upon dilution and wherein said anionic is fatty acid soap; and
(d) from about 0.1% to 90% of a hydrophilic structural dispersant comprising alkylene glycol;
wherein the deposition enhancement system further comprises oil/emollient enveloping/surrounding said optical modifier; and/or comprises oil/emollient which forms an emulsion system in which optical modifier particles are emulsified in the oil/emollient or are enveloped by the oil/emollient during dilution with water.

12. A rinse-off bar or liquid composition for delivery of enhanced visual benefits to the skin with specific optical attributes consisting of:
(a) from about 0.5% to about 90% of by wt. surfactant comprising soap and alkyl sulfate;
(b) from 0.1 to 35% by wt. of solid particulate optical modifier which exhibits a specific set of optical properties, defined by ΔL, Δa*, Δb*, change in reflectivity and/or change in opacity, and which, in combination with a deposition enhancement system, provides at least 5% change in at least one of said optical properties being targeted when said composition is applied to the skin;

(c) from 0.1 to 25% by wt. of a deposition enhancement system comprising (i) 0.1 to 10% by wt. of a polyquaternium 6 cationic polymer or polymers having an average charge density of about 6.2 meq/g; and (ii) anionic surfactant which forms precipitate with said cationic polymer or polymers upon dilution and selected from the group consisting of soap, alkyl sulfates and mixtures thereof; and (d) from about 0.1% to 90% of a hydrophilic structural dispersant comprising sugar and maltodextrin;

wherein the deposition enhancement system further comprises oil/emollient enveloping/surrounding said optical modifier; and/or comprises oil/emollient which forms an emulsion system in which optical modifier particles are emulsified in the oil/emollient or are enveloped by the oil/emollient during dilution with water.

* * * * *